(12) United States Patent
Setzer

(10) Patent No.: US 6,253,617 B1
(45) Date of Patent: Jul. 3, 2001

(54) PROCESS FOR TESTING THE FREEZE-THAW RESISTANCE OF SOLIDS

(76) Inventor: Max I. Setzer, Vittinghoffstr. 26, 45134, Essen (DE)

( * ) Notice: Subject to any disclaimer, the term of this patent is extended or adjusted under 35 U.S.C. 154(b) by 0 days.

(21) Appl. No.: 09/214,064

(22) PCT Filed: Jun. 19, 1997

(86) PCT No.: PCT/EP97/03217

§ 371 Date: Dec. 28, 1998

§ 102(e) Date: Dec. 28, 1998

(87) PCT Pub. No.: WO98/00710

PCT Pub. Date: Jan. 8, 1998

(30) Foreign Application Priority Data

Jun. 28, 1996 (DE) ............................................. 196 26 111

(51) Int. Cl.[7] .................................................. G01H 5/00
(52) U.S. Cl. ................................................ 73/597; 73/766
(58) Field of Search ............................... 73/577, 579, 799

(56) References Cited

U.S. PATENT DOCUMENTS

| | | | |
|---|---|---|---|
| 3,504,532 | * 4/1970 | Muenow et al. | 73/579 |
| 4,283,956 | * 8/1981 | Lechner et al. | 73/799 |
| 4,315,044 | * 2/1982 | Elmore et al. | 427/386 |
| 5,530,056 | * 6/1996 | Farwaha et al. | 524/558 |
| 6,031,041 | * 2/2000 | Chung et al. | 524/507 |

FOREIGN PATENT DOCUMENTS 3928130  2/1991 (DE).

* cited by examiner

Primary Examiner—Max Noori
(74) Attorney, Agent, or Firm—Fay, Sharpe, Fagan, Minnich & McKee, LLP

(57) ABSTRACT

A solid to be tested is preconditioned by drying it to a specified moisture content and its load surface is inserted downward into a test container which takes up test liquid thereby completely wetting the load surface. The test container is immersed in a temperature equalization bath which is temperature controlled. The test liquid is subjected to a predetermined temperature-time profile simulating a freeze-thaw cycle via the temperature-equalization bath. Then, at least one comparison measurement is taken to determine a change in a physical quantity representative of the inner damage to the solid. From the comparative physical values measured, the inner damage to the solid is determined based on the effects of the freeze-thaw cycle and the test liquid.

13 Claims, 3 Drawing Sheets

PROCESS FOR TESTING THE FREEZE-THAW RESISTANCE OF SOLIDS

Figure 1:
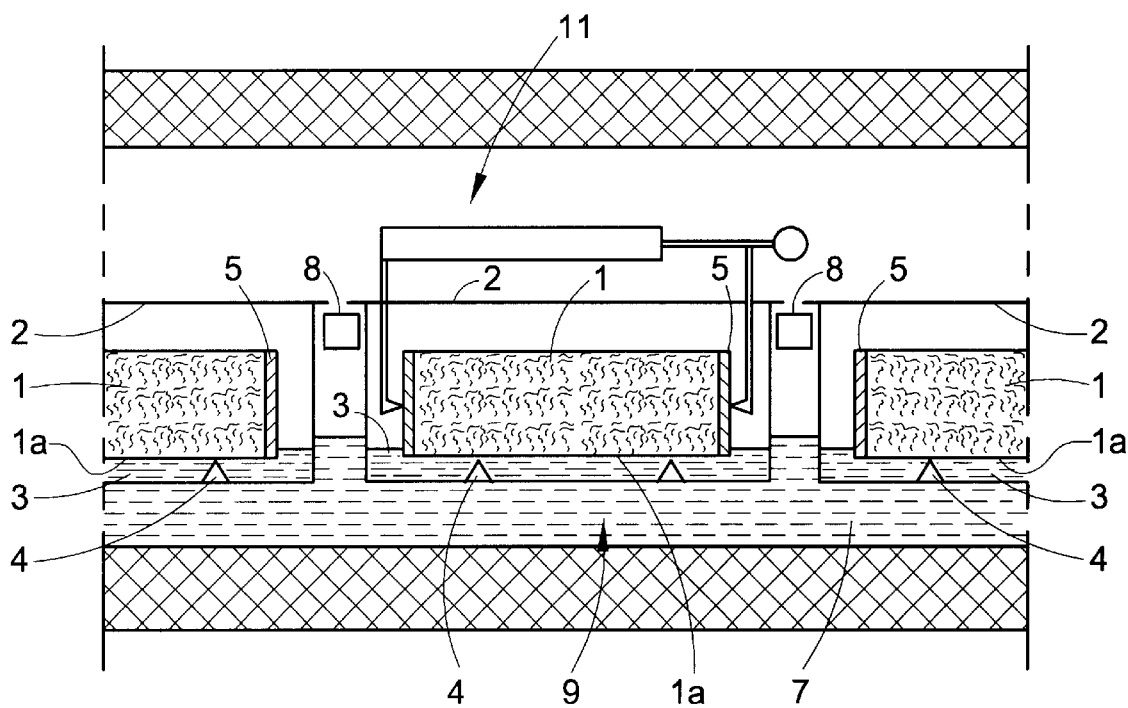

The invention concerns a method for testing the freeze-thaw resistance and/or the freeze-thaw and deicing agent resistance of solid bodies. In particular, the invention deals with an enlargement of and supplementation of a known test method for the freeze-thaw resistance or of the freeze thaw and de-icing agent resistance, respectively.

In civil engineering, materials, solid bodies or construction components are frequently subjected to attack by special environmental conditions. Typical forms of attack by the environment are freeze-thaw cycles with and without the effect of de-icing agents. In the former case, the solid bodies exposed to environmental attack require an enhanced freeze-thaw resistance; in the latter case an enhanced freeze-thaw and de-icing agent resistance. As already mentioned in the starting publication the term "enhanced freeze-thaw and de-icing agent resistance" can be applied without restriction to aqueous solutions, as far as the test method described here is concerned.

The resistance test for porous solid bodies comprises two test method stages:

1. The simulation of the external attack corresponding to the environmental attack; and
2. the measurement or the determination of the damage to the solid body resulting from this external attack.

When determining the damage, two types of damage can be distinguished:

a) The external damage, in particular the scaling; and
b) the internal damage which is rarely outwardly visible and which considerably reduces several materials properties, for example strength and elasticity.

Both types of damage occur at or near the exposed surfaces. The internal damage is also usually limited to a zone in the region of the surface under attack or starts from the surface of exposure. However in the case of internal damage, the transition from the damaged to the undamaged region is continuous. Thus it is extremely difficult to specify reproducible precise criteria, which should be universally applicable to a whole group of materials, for the internal damage.

The test method described in the starting publication is concerned in particular with the external damage or the degree of scaling. The accuracy and reproducibility of this test method were improved by guaranteeing that the specimens under investigation are a defined content of water, with or without dissolved substances, i.e. de-icing agent. For this purpose, the solid body is conditioned, in particular pre-dried, before commencement of the actual test method. Afterwards, the specimens with the exposure surfaces are immersed in the solution or water. The solution or water is then allowed to penetrate into the specimens by capillary suction. This is followed by freeze-thaw cycles to simulate the attack by freeze-thaw or freeze-thaw and de-icing agent.

So far, the known method and the improved test method, as given by the present invention, correspond to a large degree.

It is the object of the present invention to provide a test method of the kind specified in the beginning, with which the internal damage of the solid body or the specimen can also be determined with high accuracy and reproducible results.

In accordance with the invention this object is accomplished by a method for testing at least one resistance of the group consisting of the freeze-thaw resistance and the de-icing agent resistance of solid bodies, forming test specimens, the method comprising several steps. The first step includes conditioning at least one test specimen by adjusting a defined moisture condition to the ensuing conditions of use. Next, the conditioned solid body having a surface of exposure is placed into a specimen container for at test medium in such a manner that the surface of exposure is downwardly faced and is in close contact with the test medium. The specimen is immersed in a coolant bath deeply enough to provide a good and uniform thermal contact between the coolant bath and test medium. Contact is maintained between the solid body and the test medium long enough to reach a defined degree of saturation of the solid body. The test medium above the coolant bath is subjected to a predetermined temperature-time profile to simulate a continuous freeze-thaw cycle in the solid body. The test specimen is held throughout the preceding steps in the specimen container in such a manner that moisture as well as heat are transported uniaxially and substantially perpendicular to the surface of exposure into the body. At least one reference measurement is carried out to determine the change of a physical quantity of a solid body before and after the preceding steps, whereby the internal damage of said body owing to the preceding attacks by freeze-thaw cycles and said test medium is determined.

The simulation of the conditions of attack is particularly good because heat or coldness is supplied uniaxially across the surface of exposure.

The internal damage of a solid body, subjected to freeze-thaw cycles as in the described methods, is expressed, as has been established in investigations, particularly by the following physical quantities:

Decrease in strength, irreversible changes in length, decrease in the static modulus of elasticity, decrease in the dynamic modulus of elasticity, change in the damping of the dynamic modulus of elasticity and change in propagation of an ultrasonic signal.

Thus at least one of these physical quantities is measured according to the invention. The results of the measurement of the complete test method are reproducible and repeatable according to the criteria of ISO 5725 and enable a reliable quantification of the internal damage.

The invention is, however, not limited to a particular measuring method. The choice of the measuring method used depends on the particular conditions of use and accuracy requirements. It is possible to use known or newly developed measuring methods which enable the measurement of the physical quantity at least in the region of the location of use, or in the environment of the testing equipment.

The following measuring methods can be used, without claiming completeness, to determine the internal damage:

A. Measurement of Strength Reduction

The compressive strength, flexural tensile strength, the splitting strength or a similar strength quantity is measured destructively on non-exposed reference specimens and the treated specimens. This method is expensive and complicated and has the disadvantage that a specimen can only be compared once with the reference specimen and is finally destroyed afterwards. A control of the change of the damage in the different phases of the freeze thaw test is not possible.

B. Measuring of the Static Modulus of Elasticity

The static modulus of elasticity can be investigated by a suitable test loading machine. However, porous solids, especially concrete, do not deform only elastically but also plastically. Therefore, any loading leads to a irreversible deformation. Additionally, the modulus of elasticity of concrete is not linear and, thus a minimum load is necessary.

The decrease of the static modulus of elasticity caused by frost action is directly coupled with a transgression of the critical degree of water saturation. If the critical degree of saturation is reached the modulus of elasticity decreases significantly after a few freeze thaw cycles.

C. Measuring of the Dynamic Modulus of Elasticity

The dynamic modulus of elasticity, and here the real and imaginary part, can be measured in different ways.

C.1 Measuring of the Self-Oscillations (Eigen-Vibrations)

A proved method is the measuring of the self-oscillations of a given test beam. In a suitable way, for instance with an hammer, the self-oscillation is generated. Preferably, the first ground vibration is excited. It is meaningful if the hammer is equipped with an accelerometer, by which the loading can be applied reproducibly. Out of the self-oscillation the modulus of elasticity can be calculated.

If the test beam is excited to an self-oscillation and if it is at the same time supported in such a way that it is swinging without damping, then besides the natural vibrationthe damping can be measured as well. This can be done by supporting the test specimen in the nodal points for example by two piano strings. By a suitable evaluation method such as recording the decay curve or by a Fourier analyzer both can be found the natural frequencyand the damping.

C.2 Measuring of the Dynamic Modulus of Elasticity with the Aim of Ultrasonics

With the aim of ultrasonics the dynamic modulus of elasticity can be measured in two ways.

1. By exciting a self-oscillation.
2. By measuring the ultrasonic transit time of a longitudinal or transversal wave.

The measuring of the ultrasonic transit time has the big advantage that the sound wave can pass the specimen in a directed way and this both horizontally and vertically to the surface under attack. Damping can be found in this way as well dependent on the specific direction.

D. Measuring of the Irreversible Thermal Expansion.

An internal frost damage is always linked with an irreversible thermal expansion. One possibility to detect the frost damage is to measure the thermal expansion by suitable measuring marks at given locations.

E. Measuring of the Direction of an Ultrasonic Signal.

As a rule, the internal damage of a solid is inhomogeneous and starts at a surface under attack. In a method in accordance with the invention a layered damage parallel to the surface under attack is especially pronounced. Following the internal damage the sound velocity changes and an ultrasonic signal which enters under a certain angle changes its direction of propagation. In accordance with the invention this is used to measure the internal damage.

F. Measuring of a Surface Acoustic Wave.

It is well known to measure the damage of natural stones by exciting surface acoustic waves. Surface acoustic waves are generated in that the ultrasonic signal meets the measured surface via a contact medium under a defined angle. It is the critical angle for total reflection. Due to this Ralley-waves are generated at the surface of the test specimen which are then emitted under the same angle into a receiver.

As has been found by the invention, this measurement is especially well suited to detect the damage, also the internal damage of solids within the procedural step e). Herein, the known arrangement can be used with high advantages.

In accordance with the invention as especially high degree of precision of the measuring of the internal damage of a solid can be achieved by a measuring method combining the irreversible length change of the tested solid and a comparative ultrasonic measurement.

In a preferred further development of the invention, measuring plates are placed preferably at the lateral faces of the test specimen in such a way that they cannot be scaled off. The measuring plates positioned at opposite faces can be used to measure the irreversible expansion during a frost attack. It is even possible to evaluate the different length changes at the top and at the bottom of the test specimen under control. If plane measuring plates are used an ultrasonic signal can be coupled in optimally, so that transit time and damping of an ultrasonic signal can be evaluated precisely. In this way the dynamic modulus of elasticity and/or its damping can be measured dependent on the specific direction i.e. especially parallel or vertically to the surface under attack. To ensure that the heat delivery and removal of the test specimen and equivalently the capillary suction is uniaxial, the lateral faces of the test specimen are sealed in a preferred improvement of the invention whereas the surface under attack remains unsealed.

Figure 2:
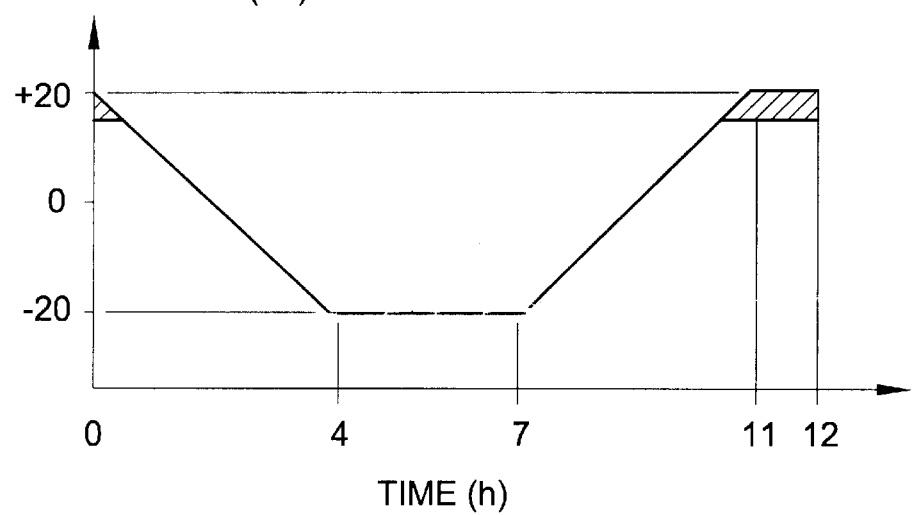
Figure 3:
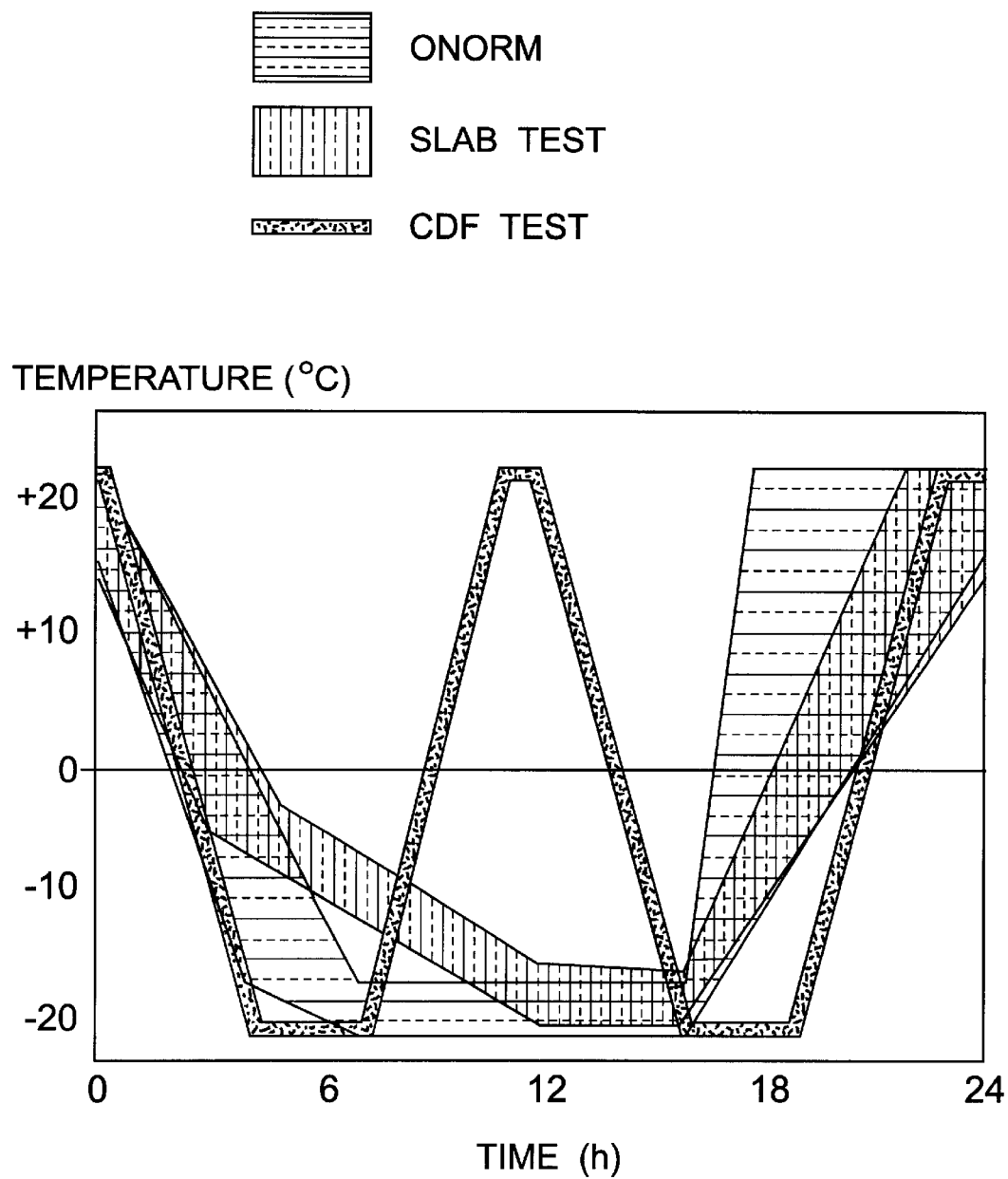
Figure 4:
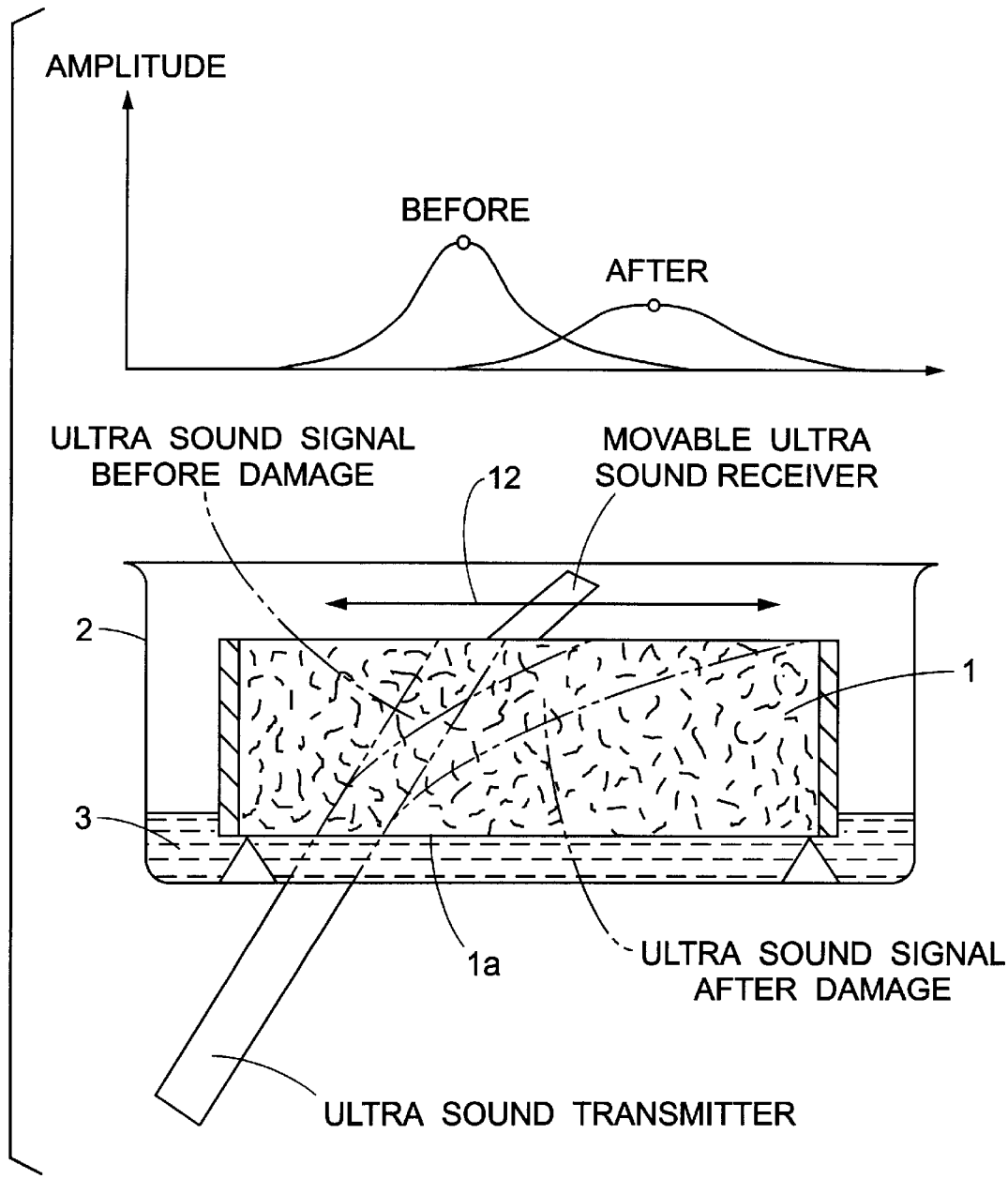

In the following context the invention is more closely explained by a drawing of the plotted test arrangement. The figure shows:

FIG. 1 is a schematic view of test arrangement by which the method of the present invention can be explained;

FIG. 2 A temperature-time diagram, which shows a typical temperature cycle during the freeze thaw attack of a solid in the test arrangement following FIG. 1;

FIG. 3 A temperature-time diagram of the attack of an freeze thaw cycle in the test arrangement following FIG. 1 compared with a common test arrangement or the simulation of a freeze that attack respectively;

FIG. 4 The schematic plot of a ultrasonic measuring arrangement to evaluate the internal damage of a solid, which is placed in a specimen container especially prepared and suited for a test arrangement following FIG. 1.

The test arrangement plotted in FIG. 1 as a schematic partial view is similar to a known arrangement.

The solid to be tested is conditioned to the following operational terms before it is put into the test arrangement following FIG. 1. This is done according to the preferred operational example of the invention in such a way that the tested solid—in the following called test specimen—is pre-dried in a defined climate until a fixed wetting condition is reached. The pre-drying can already be done in an accessory test containment 2.

In the test containment the test specimens are positioned with the surface under attack 1a at the bottom side and this in such a way that the surface under attack is just immersing into the test liquid 3 or is wetted by it. The position of the surface under attack 1a is defined by the supports 4 outlined in the operational example of FIG. 1. The level of the test liquid 3 can be adjusted using a level regulator which is not plotted in the drawing.

In the operational example shown in FIG. 1 the side faces of the test specimen 1 are sealed by a coating which is essentially scaling resistant. This guarantees that the test liquid 3 can enter only at the bottom side, however, not at the lateral pores of the solid. Therefore, the test liquid can only infiltrate the test specimen 1 by capillary suction from the bottom side via the surface under attack. This is an essential prerequisite that the test liquid penetrates the test specimen until a defined degree of saturation of the solid is reached already before the cyclic freeze thaw attack.

After the conditioning the test specimens are subjected to a well-defined cyclic freeze thaw attack in the test arrangement following FIG. 1. The heat delivery and removal is managed in an extremely advantageous way by a regulated temperature bath 7, into which all test containers 2 are immersed just so deeply that a good and uniform thermal contact between the temperature bath 7 and the test liquid 3 is reached. The immersion depth of the container 2 into the temperature bath can be varied if necessary by supports 8 which are variable in height. The cooling and heating elements of temperature bath 7 as well as the regulating equipment are not plotted in FIG. 1. Also the components for movement and circulation of the liquid in the temperature bath are not plotted in FIG. 1 as well; they can be made in common way.

The temperature bath 7 is subjected to a given temperature-time profile to simulate a freeze thaw cycle in the solid 1 as it is plotted in FIG. 1 for a time of 12 hours as an example. The temperature of the temperature bath is monitored at well-defined positions for example centrally under the test container 2 as shown in FIG. 1 by an arrow.

As outlined above a uniaxial heat delivery and removal from the temperature bath 7 via the bottom area of test container 2 and the surface under attack 1a of the test specimen 1 is achieved. This heat exchange takes place with a high efficiency due to the optimal conditions of thermal conductivity in such a way that the regulated temperature profile following FIG. 2 can be transferred to the test specimen 1 relatively fast, uniformly and with high precision of regulation.

In FIG. 3 there are plotted three different temperature cycles with mean width of variation for three different test methods. It is to be seen that the test methods used previously (ÖNORM and Slab test) have a essentially larger temperature-time variation compared to the CDF test which is used in accordance with the invention and are equivalently less precise and more time consuming. Basically, within a temperature cycle of a conventional test method several temperature cycles can be run in the test method which is in accordance with the invention (CDF test); in FIG. 3 two CDF cycles are shown.

The examination of damage of the test specimens is preferably done outside the test arrangement following FIG. 1 in a suitable test arrangement. This is especially valid for the measuring of the external scaling. For this purpose the container 2 with the test specimen 1 is removed from the test arrangement following FIG. 1 and excited during a given time by an ultrasonic bath. The scaling is collected at the bottom of the test container 2. The test liquid is decanted from the test container; the complete solid residue is dried and weighed. Dependent on the size of the body the external damage of the test specimen is given by the weight of the so found solid residue.

In FIG. 1 an arrangement for measuring length changes 11 is schematically plotted, by which the length and the length changes of the test specimen 1 can be measured at opposite sides. The arrangement of length measurement 11 is shown here in the test arrangement; of course, the test specimen can be taken out of the container 2 and put into a suitable arrangement for length measuring to evaluate the length and length change. The measurement of the values can be done—differently from the plot in FIG. 1—in several levels one above the other, especially to associate the differences in the irreversible length changes to the different layers of the test specimen. In addition, it can be appropriate to measure the length changes of the specimens 1 before and after the cyclic freeze thaw attack in several octagonal directions to evaluate the degree of internal damage of the body more precisely and dependent on the direction. The sealing coatings 5 can also be suitable plate shaped bodies which on one side can define the measuring points for length measuring more precisely and on the other side can be used as sound emission devices for ultrasonic transit time.

For the evaluation of internal damage the other methods can be used which are denominated in the introduction of the description.

In FIG. 4 a special and a such new measuring method to evaluate the internal damage of test specimens 1 is shown.

An ultrasonic signal is emitted from an ultrasonic transmitter oblique to the surface under attack 1a. Before a freeze thaw cyclic attack the test specimen is undamaged and the ultrasonic signal exits the upper side of the specimen under an angle which is equivalent to the angle of incidence. Above the container the noise intensity at the exiting point is plotted in an amplitude path diagram. After the cyclic freeze thaw attack the test specimen is damaged. The degree of internal damage is expressed in the degree of deviation of the ultrasonic signal and by this by the geometric location of the exiting point from the test specimen. As the diagram of amplitudes shows the test container shows the maximum value of the amplitude after the cyclic freeze thaw attack is remarkably shifted. From the distance of the two maximum values the degree of internal damage of the test specimens can be evaluated relatively precise. As ultrasonic receiver in the arrangement following FIG. 4 a receiver is used which is positioned on a slide and movable parallel to the upper side of the test specimen in the direction of the double arrow 12.

It is clear that different well-known measuring arrangements can be used to evaluate the physical parameters which are representative for the internal damage of the solid. By measuring the physical quantities in several different directions and/or in parallel layers and/or by using different measuring techniques the internal damage can be evaluated in a precision which has not been reached up to now.

What is claimed is:

1. A method for testing at least one resistance of the group consisting of the freeze-thaw resistance and the de-icing agent resistance of solid bodies, forming test specimens, said method comprising the following steps:
 a) conditioning at least one solid body, forming a test specimen by adjusting a defined moisture condition to ensuing conditions of use;
 b) placing the conditioned solid body having a surface of exposure into a specimen container for a test medium in such a manner that the surface of exposure is downwardly faced and is in close contact with the test medium, said specimen being immersed in a coolant bath deeply enough to provide a good and uniform thermal contact between said coolant bath and said test medium;
 c) maintaining a contact between the solid body and the test medium long enough to reach a defined degree of saturation of the solid body;
 d) subjecting the test medium above the coolant bath to a predetermined temperature-time profile to simulate a continuous freeze-thaw cycle in the solid body, wherein the test specimen is held during method steps b) through d) in the specimen container in such a manner that moisture as well as heat are transported uniaxially and substantially perpendicular to the surface of exposure into the body; and
 e) carrying out at least one reference measurement to determine the change of a physical quantity of a solid body before and after the method steps b) through d), whereby internal damage of said solid body owing to attacks by freeze-thaw cycles and said test medium is determined.

2. The method according to claim 1, wherein during said method step e) at least one of the following changes in physical quantities is determined:
- decrease in strength;
- irreversible change in length;
- decrease in static modulus of elasticity;
- decrease in dynamic modulus of elasticity;
- change in damping of the dynamic modulus of elasticity,
- change of the direction of propagation of an ultrasonic signal.

3. The method according to claim 2, wherein said solid body is thrown into its natural vibrations and wherein at least one of the physical quantities consisting of the dynamic modulus of elasticity and its damping is derived from said vibrations.

4. The method according to claim 2, characterized in that ultrasonic waves are coupled into the solid body and their transit time is measured and that at least one of the physical quantities consisting of the dynamic modulus of elasticity and its damping is derived from said ultrasonic transit time.

5. The method according to claim 1, wherein the solid body held in contact with a test medium is subjected to a freeze-thaw cycle, and wherein the solid body, before and after freeze-thaw cycles, is subjected to a comparative length measurement to determine irreversible change in length of the solid body as well as a comparative ultrasonic measurement, wherein measuring plates are mounted on two opposite surfaces of the solid body, especially on two lateral faces, in such a manner that they are not able to undergo scaling and that a change in at least one of the physical quantities consisting of the dynamic modulus of elasticity and its damping is determined from the comparative ultrasonic measurement.

6. The method according to claim 1, wherein the test specimen is sealed in such a manner that the test medium cannot penetrate into sides of the specimen whilst the surface of exposure remains unsealed.

7. The method according to claim 2, wherein at least one of the physical quantities consisting of the dynamic modulus of elasticity and its damping is determined parallel to the surface of exposure, in such a way that the ultrasonic signal passes a tested body in a given direction and that ultrasonic transit time is determined in said parallel direction.

8. The method according to claim 2, wherein at least one of the physical quantities consisting of the dynamic modulus of elasticity and its damping is determined perpendicular to the surface of exposure, in such a way that the ultrasonic signal passes a tested body in a given direction and that ultrasonic transit time is determined in said perpendicular direction.

9. The method according to claim 2, wherein the irreversible length change is determined in dependence on a direction parallel to said surface of exposure.

10. The method according to claim 2, wherein the irreversible length change is determined in dependence on a direction perpendicular to said surface of exposure.

11. The method according to claim 1, wherein a test liquid, which wets the surface of exposure of the solid body, is used as a test medium.

12. The method according to claim 1, characterized in that the test medium contains a porous storage medium and a test liquid stored therein.

13. The method according to claim 1, wherein the internal damage of the solid body is determined by the measurement of the change in direction of propagation of an ultrasonic signal in the solid body.

* * * * *